(12) United States Patent
Silver et al.

(10) Patent No.: US 11,191,999 B2
(45) Date of Patent: Dec. 7, 2021

(54) METHOD OF ALLOWING A USER TO RECEIVE INFORMATION ASSOCIATED WITH A GOAL

(71) Applicants: Adam Silver, San Francisco, CA (US); Heron Da Silva Ramos, San Francisco, CA (US); Abhishek Rahim Dewan, Sunnyvale, CA (US); Syyean Hwu Gastelum, Santa Clara, CA (US); Joo Hyun Bae, San Jose, CA (US); Jae Namkung, San Jose, CA (US); Shengjie Zhang, Santa Clara, CA (US); Michael Oliver McCann, San Francisco, CA (US); Tussanee Garcia-Shelton, Mateo, CA (US)

(72) Inventors: Adam Silver, San Francisco, CA (US); Heron Da Silva Ramos, San Francisco, CA (US); Abhishek Rahim Dewan, Sunnyvale, CA (US); Syyean Hwu Gastelum, Santa Clara, CA (US); Joo Hyun Bae, San Jose, CA (US); Jae Namkung, San Jose, CA (US); Shengjie Zhang, Santa Clara, CA (US); Michael Oliver McCann, San Francisco, CA (US); Tussanee Garcia-Shelton, Mateo, CA (US)

(73) Assignee: Samsung Electronics Co. Ltd., Suwon-si (KR)

( * ) Notice: Subject to any disclaimer, the term of this patent is extended or adjusted under 35 U.S.C. 154(b) by 383 days.

(21) Appl. No.: 15/716,624

(22) Filed: Sep. 27, 2017

(65) Prior Publication Data
US 2018/0178063 A1    Jun. 28, 2018

Related U.S. Application Data

(60) Provisional application No. 62/438,426, filed on Dec. 22, 2016.

(51) Int. Cl.
*A63B 24/00* (2006.01)
*G16H 20/30* (2018.01)
*G16H 40/67* (2018.01)

(52) U.S. Cl.
CPC ...... *A63B 24/0062* (2013.01); *A63B 24/0075* (2013.01); *G16H 20/30* (2018.01);
(Continued)

(58) Field of Classification Search
CPC .. A63B 24/0062; A61B 5/1118; G06Q 50/01; H04L 67/306; G09B 19/003; G09B 19/0038
See application file for complete search history.

(56) References Cited

U.S. PATENT DOCUMENTS 8,777,624 B2   7/2014   Klein
8,951,165 B2   2/2015   Morris
(Continued)

FOREIGN PATENT DOCUMENTS

WO   2010/138975   12/2010
WO   2011143513    11/2011
(Continued)

OTHER PUBLICATIONS

EP Appl. 178855244.8 (PCT/KR2017015191) Supplementary European Search Report, dated Dec. 20, 2019.
(Continued)

*Primary Examiner* — Peter R Egloff
(74) *Attorney, Agent, or Firm* — John J. King

(57) ABSTRACT

A method of allowing a user, using a wellness tracking device, to receive information associated with a wellness goal is described. The method comprises presenting at least one other user for the user to follow; allowing the user to select a user of the at least one other user to compare
(Continued)

wellness information; and providing, to the user, the information related to wellness activities of the selected user.

20 Claims, 14 Drawing Sheets

(52) U.S. Cl.
CPC .......... *G16H 40/67* (2018.01); *A63B 24/0084* (2013.01); *A63B 2024/0065* (2013.01); *A63B 2024/0068* (2013.01)

(56) References Cited

U.S. PATENT DOCUMENTS

| | | | |
|---|---|---|---|
| 9,794,752 B1* | 10/2017 | Doherty | .................. H04W 4/08 |
| 2006/0205564 A1 | 9/2006 | Peterson | |
| 2008/0096726 A1* | 4/2008 | Riley | .................. A63B 24/0006 |
| | | | 482/8 |
| 2010/0331146 A1 | 12/2010 | Kil | |
| 2011/0015495 A1 | 1/2011 | Dothie | |
| 2011/0143513 A1 | 6/2011 | Krutsick | |
| 2011/0161107 A1 | 6/2011 | Goldberg | |
| 2011/0246926 A1 | 10/2011 | Newton | |
| 2013/0089840 A1 | 4/2013 | Drane | |
| 2013/0124218 A1 | 5/2013 | Masloski | |
| 2014/0038781 A1* | 2/2014 | Foley | .................. A63B 24/0075 |
| | | | 482/9 |
| 2014/0052280 A1 | 2/2014 | Yuen | |
| 2014/0125480 A1 | 5/2014 | Utter, II | |
| 2014/0142967 A1 | 5/2014 | Bedrosian | |
| 2014/0274404 A1* | 9/2014 | Hoskins | .................. A63F 13/795 |
| | | | 463/42 |
| 2014/0288448 A1 | 9/2014 | Saalasti | |
| 2014/0316305 A1* | 10/2014 | Venkatraman | .......... A61B 5/681 |
| | | | 600/595 |
| 2015/0139615 A1* | 5/2015 | Hill | .................... H04N 21/2743 |
| | | | 386/285 |
| 2015/0281384 A1 | 10/2015 | Gunnarsson | |
| 2015/0289812 A1 | 10/2015 | Pacione | |
| 2015/0347700 A1 | 12/2015 | Shariff | |
| 2017/0289302 A1* | 10/2017 | Chander | .................. G09B 7/02 |
| 2017/0301258 A1* | 10/2017 | Ram | ........................ G09B 5/02 |

FOREIGN PATENT DOCUMENTS

| | | |
|---|---|---|
| WO | 2013142069 | 9/2013 |
| WO | 2015183849 | 3/2015 |
| WO | 2015048683 | 4/2015 |

OTHER PUBLICATIONS

Munson, "Beyond the Share Button: Making Social Network Sites Work for Health and Wellness," IEEE Potentials, vol. 30, No. 5, Sep. 1, 2001.

* cited by examiner

1102 — Time zone shift: Activity ✗

Staying active when moving between time zones can be challenging. Learn how to maintain your activity goals in Taipei.

REVIEW GOAL

Time zone change

You currently have 4 hours of daylight left to meet your activity goals in Taipei.

1104

Social insight

The most active period for S Health users in Taipei is from 3:00 PM- 6:00 PM.

1106

VIEW DETAILS

FIG. 11

METHOD OF ALLOWING A USER TO RECEIVE INFORMATION ASSOCIATED WITH A GOAL

FIELD OF THE INVENTION

Embodiments of the present invention relate generally to information and/or activity tracking, and in particular, to a method of allowing a user to receive information associated with a wellness goal.

BACKGROUND OF THE INVENTION

Consumer health apps have seen a gradual decline in interest and usage over the past few years due to a fundamental misunderstanding of their value to consumers. Most have operated under the assumption that users already have clearly-defined health goals, that they understand how to interpret data and enjoy doing it, that they are highly motivated and involved in managing their own health, and that their time is relatively free and available. Many users do not fall into these categories, and are underserved by current market solutions. They may have interest in improving their health, but many do not have clearly defined goals, an understanding of how to take small, progressive steps towards their goals, a love of data and numbers, or the time to micro-manage their decision marking.

SUMMARY OF THE INVENTION

A method of allowing a user, using a tracking device, to receive information associated with a goal is described. The method comprises presenting at least one other user for the user to follow; allowing the user to select a user of the at least one other user to compare information; and providing, to the user, the information related to activities of the selected user.

Another method of allowing a user, using a wellness tracking device, to receive information associated with a wellness goal, comprises identifying users that are tracking wellness information; determining whether a wellness measurement of an identified user that is tracking wellness information is within range of a wellness measurement of the user; and providing a challenge to the user based upon the wellness measurement.

A further method of allowing a user, using a wellness tracking device, to receive data associated with a wellness goal, comprises determining whether a user has failed to achieve a wellness goal; initiating an intervention period to help the user to achieve the wellness goal; and providing a recommendation to the user to achieve the wellness goal.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

FIG. 11 is a diagram showing the presentation of information associated with a time zone shift;

DETAILED DESCRIPTION OF THE DRAWINGS

The systems and methods set forth below provide an intelligent engine that compares user-set goals, behavioral and sensor-driven data, a user's self-report-data, and external data sources to form correlations that help users understand the cause and effect behind their decisions, and provide information and suggest actions, also known as Actionable Insights, that might further improve their status based on this data. These correlations, information and suggestions are pushed to the user when they are believed to have the most impact, and are pushed only when a significant correlation is found or a suggestion is generated. Insights that are continually engaged with are weighted by the intelligent engine, allowing the product to push more useful information to the user over time.

The text and figures are provided solely as examples to aid the reader in understanding the invention. They are not intended and are not to be construed as limiting the scope of this invention in any manner. Although certain embodiments and examples have been provided, it will be apparent to those skilled in the art based on the disclosures herein that changes in the embodiments and examples shown may be made without departing from the scope of this invention.

While the specification includes claims defining the features of one or more implementations of the invention that are regarded as novel, it is believed that the circuits and methods will be better understood from a consideration of the description in conjunction with the drawings. While various circuits and methods are disclosed, it is to be understood that the circuits and methods are merely exemplary of the inventive arrangements, which can be embodied in various forms. Therefore, specific structural and functional details disclosed within this specification are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting, but rather to provide an understandable description of the circuits and methods.

Figure 1:
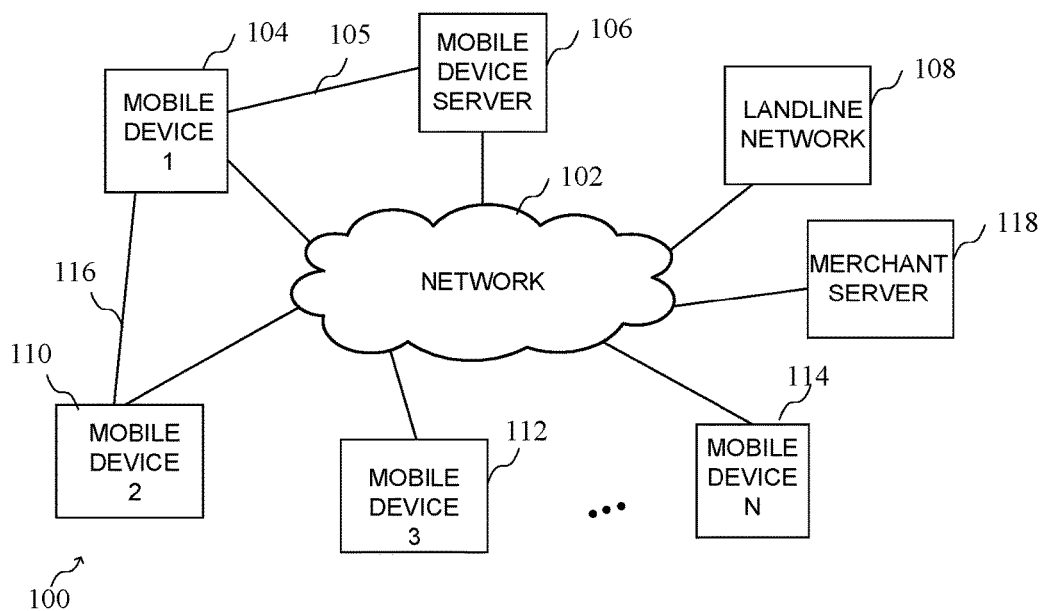
FIG. 1 is a block diagram of an exemplary system for allowing a user to receive information associated with a goal.

Turning first to FIG. 1, a block diagram of an exemplary system for allowing a user to receive information associated with a goal is shown. In one embodiment, a goal may be a wellness goal (i.e., any type of goal associated with the physical or mental well-being) of a user of a mobile device or a user participating in a wellness program designed to improve the physical or mental well-being of the user. Wellness goals could include such goals as weight loss, increased exercise, improved sleep, improved circulation, improved skin condition, improved heart rate, improved blood pressure, improved mental function, improved memory, or any other measurable, detectable, or perceived improvement in a physical or mental condition of a user.

A system 100 provides various elements associated with a network 102, which may be a wireless communication network for example. The system 100 comprises a mobile device 104 that may be coupled to a mobile device server 106 by way of a communication link 105 separate from the network 102, or by way of the network 102 using communication links between each of the mobile device 104 and the mobile device server 106 and the network 102. As will be described in more detail below, information related to a mobile device may be stored on the mobile device server 106. The mobile device server 106 may be associated with a manufacturer of the mobile device 104, and therefore be considered a trusted entity associated with the mobile device, or may be a third-party server that provides a service, such as a wellness tracking program (e.g. implemented as an app on a mobile device for example) for registered users. The network 102 could be any type of network, such as a wireless network, for transferring data between elements of the system 100. While shown as a single network, the network 102 may comprises a plurality of different networks operating using different data transfer protocols that may be controlled or operated by different network operators.

Other elements of the system may include another network, such as a landline network 108, and other mobile devices 110-114, for example. Some of the mobile devices may communicate directly with one another, such as mobile device 104 and mobile device 110, which may communicate by way of a communication link 116. The communication link 116 may be any type of communication link that provides direct communication between two elements of the system, such as two mobile devices. By way of example, the communication link 116 could be any type of local connection that does not require network 102, such as a Bluetooth connection, a Near Field Communication (NFC) connection, a WiFi connection for mobile devices that are on the same WiFi network, a cellular network separate from network 102, or any other type of communication link that would enable one or more users exchange information between mobile devices.

By way of example, mobile device 104 could be a smart phone and mobile device 110 could be a wearable device having one or more sensors for providing or receiving domain information, context information, environmental information, or any other type of information that may be useful in helping a user achieve a goal. In addition to wellness tracking, Actionable Insights could be implemented when tracking the activities of a user in other domains, such as travel, work, education, recreation, or entertainment, for example, where Actionable Insights could provide information or suggestions that improve a user's benefit or enjoyment in that particular domain. When the domain is related to health or wellness, domain information may be wellness information including biometric information associated with a user that is detected by a mobile device. Biometric information could be any data that is detected by a sensor on or associated with the mobile device, such as from a wearable device in communication with a mobile device, including for example heart rate, body temperature, skin temperature, carbon dioxide levels, oxygen levels or any other biological measurement that could be detected by a sensor. Context information may include any type of data related to time, date, a user's location, a user's schedules, a user's calendar information, location of other users registers with a program, other users' schedules or calendar information, schedule information related to facilities, including local facilities such as parks, community centers, fitness centers, athletic equipment stores, health food stores (e.g. physical locations or on-line), or other facilities or locations that may be accessed or used by a user to achieve a goal. Environmental information may include current weather information, weather forecasts, temperature, humidity, wind speed, a barometric measurement, or other information that may affect a user achieving a goal. The system may also include a merchant server 106 that could provide information related to products or services which could help a user achieve a goal.

The mobile devices could be any type of device for tracking information, and some mobile devices may be associated with a single user. By way of example, a mobile device could be a portable wireless communication device, such as a smart phone, tablet computer, or laptop computer, or a wearable device, such as smart watch, smart wristband, smart pendant, or smart necklace. Information from different mobile devices may be associated with a single user and stored on the mobile device server 106, one or more mobile devices of the user, or both. Information from multiple users associated with multiple mobile devices may be stored on the server to enable providing information associated with goals to a user of a mobile device, as will be described in more detail below. While mobile devices are shown by way of example, some information associated with one or more users may be acquired from or provided to a fixed device, such as a desktop computer having sensors or other monitoring devices for storing information from a user.

While other elements could be implemented in the system 100, the elements are shown by way of example to provide context for the use of devices that enable the tracking of information. FIG. 1 is just one example of a system for providing tracking information to a user to aid a user in achieving a goal, and different configurations of elements or additional elements could be implemented to allow a user to receive information related to a particular program, including information related to achieving a wellness goal as described below.

Figure 2:
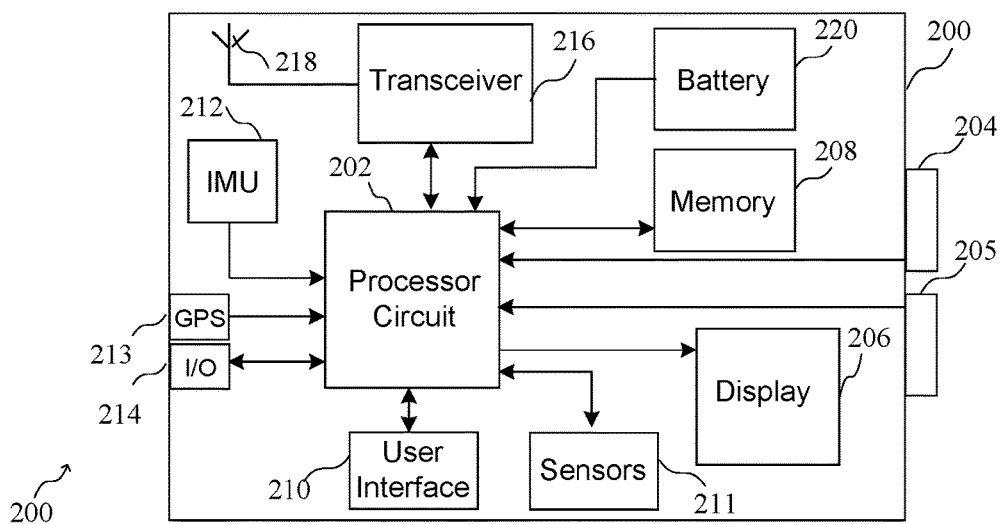
FIG. 2 is a block diagram of a mobile device that may be implemented in the system of FIG. 1.

Turning now to FIG. 2, a block diagram of an exemplary mobile device 200 that may be implemented as any of the mobile devices in the system of FIG. 1 is shown. The mobile device 200 may comprise a processor circuit 202 coupled to a plurality of cameras 204 and 205. The mobile device 200 could be any type of device adapted to transmit and receive information, such as a smart phone, tablet or other electronic device receiving or providing information, such as a wearable device. The processor circuit 202 could be an ARM processor, an X86 processor, a MIPS processor, a graphics processing unit (GPU), a general purpose GPU, or any other processor configured to execute instructions stored in a memory. The processor circuit 202 could be implemented in one or more processing devices, where the processors may be different. For example, the electronic device could include a central processing unit (CPU) as well as a GPU for example.

The processor circuit 202 may be coupled to a display 206 for displaying information to a user. The processor circuit 202 may also be coupled to a memory 208 that enables storing information related to data or information associated with achieving a goal. The memory 208 could be implemented as a part of the processor circuit 202, or could be implemented in addition to any cache memory of the processor, as is well known. The memory 208 could include any type of memory, such as a solid state drive (SSD), Flash memory, Read Only Memory (ROM) or any other memory element that provides long term memory, where the memory could be any type of internal memory of the electronic drive or external memory accessible by the electronic device. By providing a local memory, user preferences and other information which a user may desire to keep private is not compromised.

A user interface 210 is also provided to enable a user to both input data and receive data. Some activity tracking may require user's manual input. The user interface could include a touch screen user interface commonly used on a portable communication device, such as a smart phone, smart watch or tablet computer, and other input/output (I/O) elements, such as a speaker and a microphone. The user interface could also comprise devices for inputting or outputting data that could be attached to the mobile device by way of an electrical connector, or by way of a wireless connection, such as a Bluetooth or a Near Field Communication (NFC) connection. A user may also be able to log on to an account associated with an app that tracks a user's progress in achieving a goal.

The processor circuit 202 may also be coupled to other elements that receive input data or provide data, including various sensors 211, an inertial measurement unit (IMU) 212 and a Global Positioning System (GPS) device 213 for activity tracking. For example, an inertial measurement unit (IMU) 212 can provide various information related to the motion or orientation of the device, while GPS 213 provides location information associated with the device. The sensors, which may be a part of or coupled to a mobile device, may include by way of example a light intensity (e.g. ambient light or UV light) sensor, a proximity sensor, an environmental temperature sensor, a humidity sensor, a heart rate detection sensor, a galvanic skin response sensor, a skin temperature sensor, a barometer, a speedometer, an altimeter, a magnetometer, a hall sensor, a gyroscope, WiFi transceiver, or any other sensor that may provide information related to achieving a goal. The processor circuit 202 may receive input data by way of an input/output (I/O) port 214 or a transceiver 216 coupled to an antenna 218.

Figure 3:
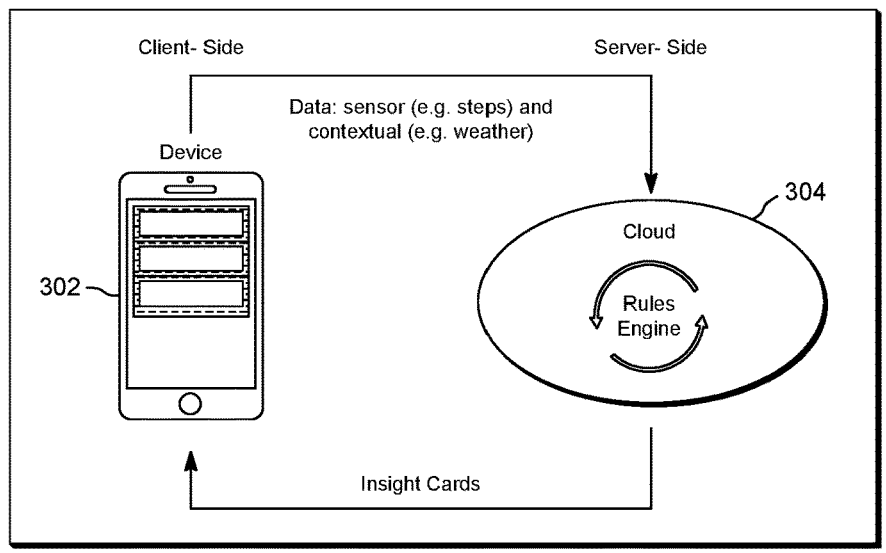
FIG. 3 is a block diagram showing an exemplary transfer of information between a client side and a server side.

Various embodiments described in the present disclosure illustrate the method and/or system for tracking information to achieve a goal using wellness as the domain. It will be appreciated by ordinary people skilled in the art that the method and/or system described are applicable to other domains. Turning now to FIG. 3, a block diagram shows a transfer of information between a client side and a server side. Users may have a device for activity tracking via sensors associated with device. The device could be smart device, such as a mobile phone, a wearable device such as a smart watch, a smart pendant, a smart bracelet, etc. As shown in FIG. 3, a client-side device 302, which may be a mobile device for example, exchanges information with a server-side device 304, which may be a cloud-based server having a rules engine, in one embodiment. Data, including for example sensor data, environmental data and contextual data, are provided to the rules engine of the server-side. A rules engine may analyze the data and generate information, such as insight information as described below to help achieve a wellness goal. Information related to a wellness program of the user, such as an insight card that could be displayed on a screen of a mobile device, can be provided back to the user, as will be described in more detail below. While an insight card is shown by way of example, it should be understood that information related to achieving a wellness goal could be provided to a user in any format, such as visual or audible format, or at any type of device, including multiple devices accessible by a user.

In addition to tracking activity, a mobile device may monitor a user's sleep or lack of activity. For example, to monitor a user's sleep, one embodiment may track data points, including but not limited to a duration of sleep, historical sleep data, a time that the user went to sleep, a time that the user woke up, a sleep consistency rating, phone usage data, weather information, heart rate, caffeine input data (e.g. a manual input), user provided sleep rating (e.g. a manual input).

Based on the tracked data, in one embodiment of the invention, three types of Actionable Insights may be presented to the user, such as by way of an insight card or some other messages, (e.g. an audible message). Actionable Insights may suggest actions for the user to take on, in view of the insight concluded based on the tracked data that may be received from a sensor, input by a user, or otherwise provided to a device of the user. Proactive insights are Actionable Insights provided to the user based on continuous tracking of the user's progress measured against their set goal. Reactive insights are Actionable Insights presented to the user based on trends being noticed by the system with respect to the goals set by the users. Noticeable trends may represent repeatable patterns that can be noticed from the historically collected user data. Such an insight is provided as a summary to the user. Correlational insights are Actionable Insights driven by combining multiple user data points into a single insight that is then presented to the user so that the user may be able to derive unseen patterns from the data. Criteria for determining whether to display an insight may include whether there is an insight or a correlation available, whether the correlation or insight is significant, the relative importance of the insight, the number of insight carts that have been displayed recently, whether it is the right time of the day to display the insight, and whether a user has found an insight card useful in the past.

Using the sleep example, one embodiment may notify the user of: 1) a reactive insight revealing a noticeable trend such as "Ten consecutive days of extra sleep . . . must feel good. Would you like to extend your sleep goal?"; 2) a proactive insight such as "It's getting to that time of the day to wind things down. Hit the zzz in the next hour to exceed your sleep goal"; and/or 3) a correlational insight such as "This is interesting: on the days that you sleep less, you walk less. Don't let today be another statistic, and hit that 8 k step goal!" While proactive insights, reactive insights, and correlational insights are shown by way of example, it should be understood that these categories are provided by way of example, and different categories or additional categories could be provided.

Figure 4:
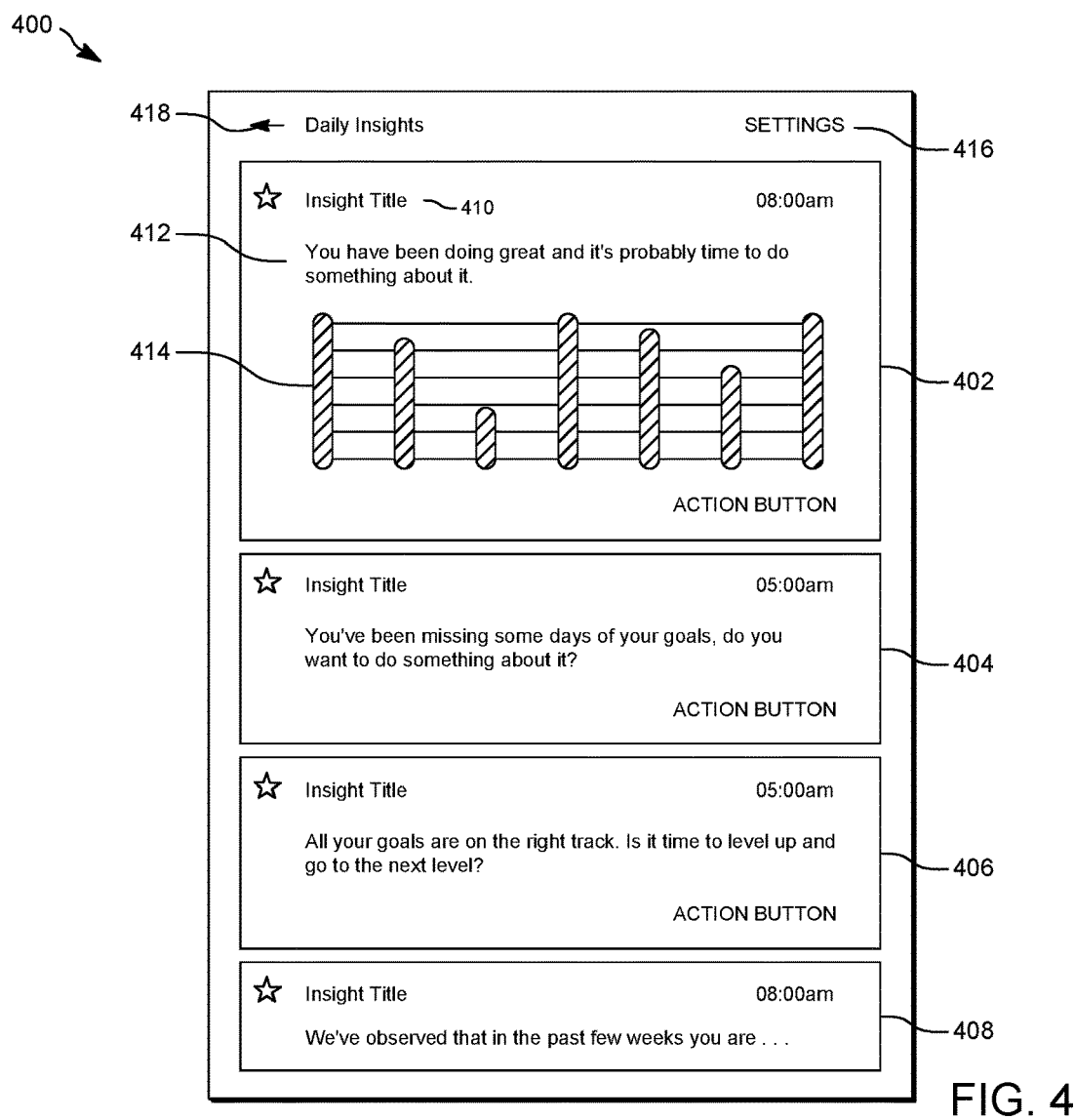
FIG. 4 shows a daily insight feed that may be provided to a user receiving wellness information.

Turning now to FIG. 4, an example of a daily insight feed 400 that may be provided to a user receiving wellness information is shown. The daily insight feed may be shown on a screen of a device of the user, or provided to the user in some other format, such as an audible format. The daily insight feed 400 may comprise a plurality of insight cards 402-408. Each insight card may include an insight title 410, an information portion 412, and a graphic portion 412. Each of the insight cards may be selected, such as by tapping on the insight card, to see additional information related to the insight. While specific fields of the insight cards are shown by way of example, it should be understood that different fields, including a lesser or greater number of fields could be implemented. The daily insight feed 400 may comprise a settings option 416, which can be selected to set preferences related to the display of insight information. A return option 418 can be selected to leave the daily insight feed.

A Social Insight is another type of insight that may be provided, and may include using a user's stated goals and friend networks to suggest competing with a friend (who may be another user registered to a wellness tracking program for example) to boost their performance and engagement level and "beat" their score for the week. The user device is configured to identify friends of the user registered to the wellness tracking program. While friends are described by way of example, a user may also follow one or more users that they do not know, which may include celebrities or other famous people. Friends of the user may be first retrieved from the contact list stored on the device. Friends of the user can be further determined, upon the user's authorization, based on the user's social network information (such as Facebook friends, Instagram followers, contacts saved in an email service, etc.). The device may connect with the wellness service and identify those friends that are also registered with the service. A wellness service could be any type of service that may help a user improve any aspect of health, such as health monitoring, or any other service that may increase the chances of achieving wellness goals, such as involvement in fitness centers that provide opportunities to exercise, or clubs or organizations for purchasing health food, exercise equipment, or electronic equipment for tracking or taking measurements of a user. Of course, a user can identify friends (registered with the wellness service) whom she would like to connect with and view their wellness achievements. In addition to identifying friends, the service can also "match" the user to a similar profile based on the aforementioned process, or identify groups or celebrities to match with. The matching capability may be performed on a wellness tracking server used by a wellness tracking program, such as a mobile device server for example.

One or more devices, such as mobile devices, monitor the user's performance, and can challenge the user based on her friend's performance retrieved from the wellness server. When the user's performance is shown to be lower than her friend's but within a reasonable or achievable threshold, the device may suggest a challenge to the user. When more than one friend has been identified, the device may choose a friend whose goal is the closest to the user, or the device may choose a friend based on frequency of interactions between the user and this friend. It can also base suggestions on currently followed users.

If the user's friend has not consented to sharing activity details with the user, the wellness service may only share some information, such as an achievement level with a device of the user. The device can determine the achievement level of the user, and based on the level difference, ask the user whether she would like to beat her friend (i.e. achieve greater performance according to one or more criteria, including for example one or more measurements based upon user tracking). The achievement level may be predetermined by the wellness service or program based on a ranking mechanism. For example, all registered users may be ranked from 1 to 10 based on activity type and length. This way, the user will not know exactly what her friend did, or for how long. However, the device is able to determine what can be done to raise levels. If the friend opts to share activity details with the user, the device can provide such details to the user. The device will notify the user that her current wellness plan or "goal" needs to be updated to beat her friend or followed users, also known as shadowed users.

The device may notify the user that her current wellness plan or "goal" needs to be updated to beat her friend. The device may make recommendations that may help the user achieve that goal. The recommendations may be as simple as carrying out one activity longer than planned. The device may also recommend alternative activities, taking into consideration environmental data such as weather, pollution, time, location, venue, and/or user's history and preference. As the user's device has access to a user's calendar and events data, the device may suggest a certain activity on a time that is effective and convenient for the user to outperform her friends. For example, the device may understand that the user will have a BBQ party near a park this weekend, and therefore recommend playing soccer so that the user can boost her performance without changing her weekend plans.

In one embodiment, if the user chooses to accept a challenge, a notification will be sent to the friend informing her that the user will try to compete, and the friend's device may make a recommendation in a similar manner to help the friend maintain the lead. If the user succeeds in the challenge, the device may ask the user to upgrade her wellness plan accordingly.

In one embodiment, the device may recommend that the user follow her friend, as a "ghost" or "shadow" user. If the user chooses to do so, the device may make recommendation in a way to mirror the friend. If the user and the friend are located in different areas, the device can map the friend's venue to a local one available to the user, based on the user's current location. For example, if the user's friend is jogging in Central Park, and the user is in Mountain View, Calif., the user's device may recommend following a trail in the Shoreline park that resembles the trail in Central Park, such as in distance, incline or overall difficulty or calories burned.

The following example illustrates a daily insight provided to a user to follow a friend. User A has set a goal to be active for at least 60 minutes a day. She meets this goal on Monday and Tuesday, but falls behind on Wednesday. A health tracking app notices her dip in performance and selects User B as a suggested challenge partner based on his similar goals and strong weekly performance. On Thursday, she receives an insight card that reads, "User B is tearing it up this week. If you walk 72 minutes for the rest of the week, you can beat his weekly score." User A taps the card and accepts the challenge, modifying her goal for the week. Each day, she receives an activity summary card showing her performance relative to User B and adjusting her daily goals to include her original goal (60 minutes) and stretch goal (72 minutes). By the end of the week, User A has surpassed her 60-minute goal and beaten User B on the weekly leaderboard. Next week, User B may challenge User A to push his goals even further.

An Intervention Insight may also be provided. When a user's goals are not successfully being achieved, a request may be made for regular self-report data to augment their sensor data, and ultimately a detailed report suggesting steps to take may be provided. When the user runs into difficulty staying on a wellness plan or "goal," the device may provide an insight card that communicates the challenge and suggests that the user start an intervention period. Intervention may have preset notions or threshold values based on medical knowledge or user history data. For example, some studies show that a person should have an average daily sleep of 7-8 hours. If the user has entered the sleep time goal from 11 PM to 7 AM, an intervention period may be triggered when the device determines that the user failed to follow her sleep schedule (for example, the user has gone to bed later and/or got up later) for a certain time period. The length of the intervention period may have a system default value, or an initial set up based on the nature of the activity. For the sleep example, the intervention period may be set as two weeks, but may generally have a finite value and last for a specific, limited period of time.

As a part of the intervention, the device may retrieve a list of survey questions associated with the difficulty experienced by the user. The list of survey questions may be created based on medical knowledge maintained at a wellness service using a wellness server or by a wellness program that helps illuminate underlying causes of failure to achieve a certain wellness plan or goal. For the sleep example, the device may ask whether the user has consumed coffee in the later afternoon, or whether the user drinks water before bedtime. The device may also ask questions related to water consumption. These questions may be asked during appropriate times during the day to coincide with the behavior being questioned (e.g. sleep questions immediately upon waking, food questions after regular meal times, etc.).

The device may recommend remedial actions, in response to the user's answer to the survey questions, or withhold making suggestions until the end of the intervention period, depending on the strength of a behavior pattern. For example, if the user indicates that she did drink espresso at 5 PM, the device may suggest drinking it earlier during the day or a decaf coffee instead at 5 PM. Remedial actions may also be suggested based on shadowed users. For example, the device may state that shadowed users found success drinking a decaf coffee at 5 PM. The alternative suggestions are also based on established medical knowledge and/or common observation. For example, if the user indicates that she drinks water right before bedtime, the device may suggest to avoid drinking water two hours before bed. For the same sleep schedule problem, and similar answers to the survey questions, the devices may recommend different options to various users due to their medical conditions, or may withhold recommendations until more conclusive suggestions are available. Each survey question may have a different prompting frequency, based on the nature of the question and/or status update of the user. Using the sleep problem as an example, the coffee question may be raised every other day, while the water question may be prompted twice a week.

If the device determines that the sleep schedule has improved, the device may further suggest a tracking program to the user. For example, the device may recommend a coffee tracker, if the user's sleeping schedule improved after stop drinking coffee in the late afternoon.

At the end of the intervention period, if the device has observed improved performance, the device may present the user with a comprehensive report of their performance relative to the type of intervention and goal (e.g. sleep, activity, nutrition, etc.). This report may combine elements of both quantitative (i.e. behavior-based) and qualitative (i.e. self-report or survey) data. Through an algorithm that observes both closed-end self-report and quantitative, sensor-gathered data, the device may generate a series of observations or patterns that have been observed, potential suggestions or ideas on ways to improve the user's health, and additional options to learn more. These suggestions may include changes to the user's goals, new goals or trackers to employ, or a suggestion to connect to a doctor using the Ask an Expert feature of a health tracking app. These actions may be related to any shadowed users, showing suggestions these users have taken.

The device may also suggest extending the intervention period to ensure that the improvement has been stabilized.

How long an intervention period can be extended may be goal-specific, and/or be determined by the nature of the recommended actions. If the device determines that the issue stays or that the device has exhausted the survey questions, the device may obtain a list of professionals that may be provided to the user and that may help the user with the difficulty experienced by the user.

The example below demonstrates an intervention initiated by a health tracking app implemented on a device of the user. User A is struggling with her sleep. Her goal is to sleep at least 7 hours a night, and she has consistently slept less than 5 for over two weeks. The device notices this pattern and suggests that she conduct an intervention to better understand her sleep habits and suggest ways for her to sleep better. User A agrees and elects to begin the intervention program. Every morning, she receives a series of prompts that ask her to rate her sleep, and ask whether certain conditions were present during her sleep. For example, the device may ask how many times she woke up during the night, whether she experienced night sweats, or whether she had trouble falling asleep. During the evening, the device may ask if her lights are still on, whether she is working or winding down, or whether she has begun to get ready to sleep. After two weeks, User A may receive a report from her device illustrating her sleep patterns, and showing that she tends to get poor sleep when she has night sweats, and that this is correlated with her caffeine intake during the day. The device may suggest that she limit caffeine to one cup of coffee before 3 pm, and adjust her caffeine tracker accordingly. User A consents and begins her new sleep program.

Figure 5:
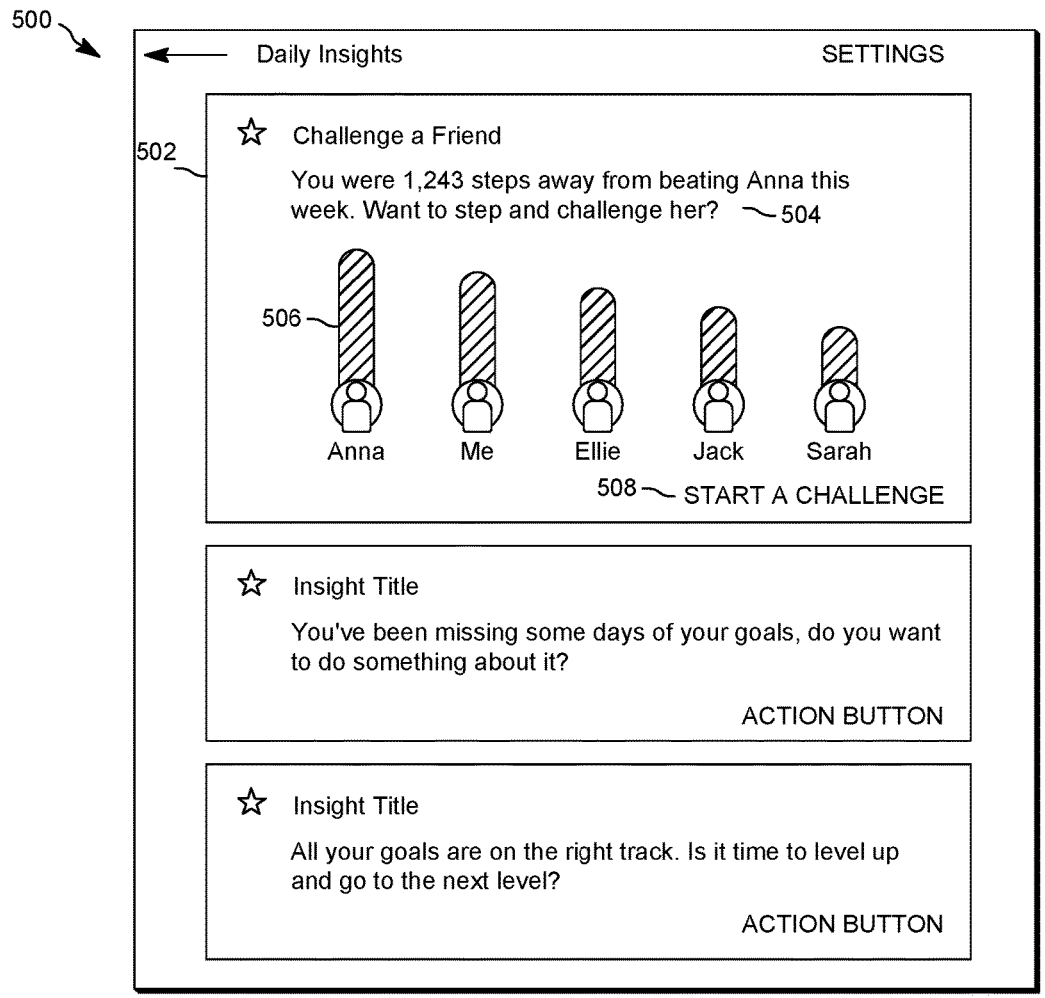
FIG. 5 shows another daily insight feed that may be provided to a user receiving wellness information.

Turning now to FIG. 5, another example of a daily insight feed 500 that may be provided to a user receiving wellness information is shown. The example of a daily insight feed shown in FIG. 5 includes an insight card comprising a challenge request 502 having an information portion 504 including a challenge related to a number of steps taken for the day, and a graphic portion 506 showing a number of steps taken by the user of the mobile device (designated at "me") and 4 other users including Anna, Ellie, Jack, and Sarah. The user can select the option 508 to accept the challenge.

Insight Cards are intended to provide the user with clear, impactful health insights in plain language, and a direct action to take to improve their health and achieve health related goals. Actionable Insights provided on insight cards can be accessed by tapping on an Insight Feed icon, which loads the Insight Feed as will be described in more detail below in reference to FIG. 7. Further, tapping on a card leads to a Detail View. Actionable Insights can also be accessed directly by tapping on a notification delivered via a Quick Panel, as will also be described in more detail below in reference to FIG. 7. Actionable Insights may be powered by a rule-based engine that compares various data (e.g. user goals, behavioral and sensor data, self-report data, external data sources) to determine triggers or correlations that drive user insights and suggests actions to improve their health.

According to some implementations, different types of data can be provided to or detected by a device used to provide wellness information to a user. By way of example, the data could include user goals, such as to "Feel More Rested: Bedtime and Wakeup Times, Sleep Quality Goal," "Be More Active: Active Minutes, Calories, Steps," or "Eat Healthier: Calories Consumed, Fat/Carbohydrates/Protein Consumed." The data could also include sensor data, which may include sound amplitude, acceleration, light intensity, screen proximity (which may be used to adjust the size of a font displayed on a screen), running apps (which may be used to how information is distributed), battery states (which may affect when and how often insights are provided), screen states (which may be used to determine what a user is doing at the time and what insights to provide), and GPS/location, for example. The data could also include Self-Report Data: Feel More Rested: Bedtime and Wakeup Times, Sleep Quality Goal, Be More Active: Active Minutes, Calories, Steps, Eat Healthier: Calories Consumed, Fat/Carbohydrates/Protein Consumed. External Data Sources could also be used to provide Weather and local conditions (e.g. UV, humidity, pollution, etc.), Friends' activity and goals (e.g. social data). While some examples of data sources are provided, it should be understood that other sources of data could also be used to determine or obtain data associated with a wellness program.

Insights may also be pushed to the user when they are believed to be most timely, and are pushed only when a significant trigger or correlation is found. Variations on the insight are displayed at random, and variations with greater engagement are prioritized for future display. User interactions may be monitored by the system and tracked. Via a Bayesian learning algorithm for example, card types that are consistently engaged with (e.g. taps, time spent) are prioritized and displayed; ignored cards are deprioritized and stop appearing. Linguistic and content-based variations are A/B tested, with favored combinations prioritized.

Figure 6:
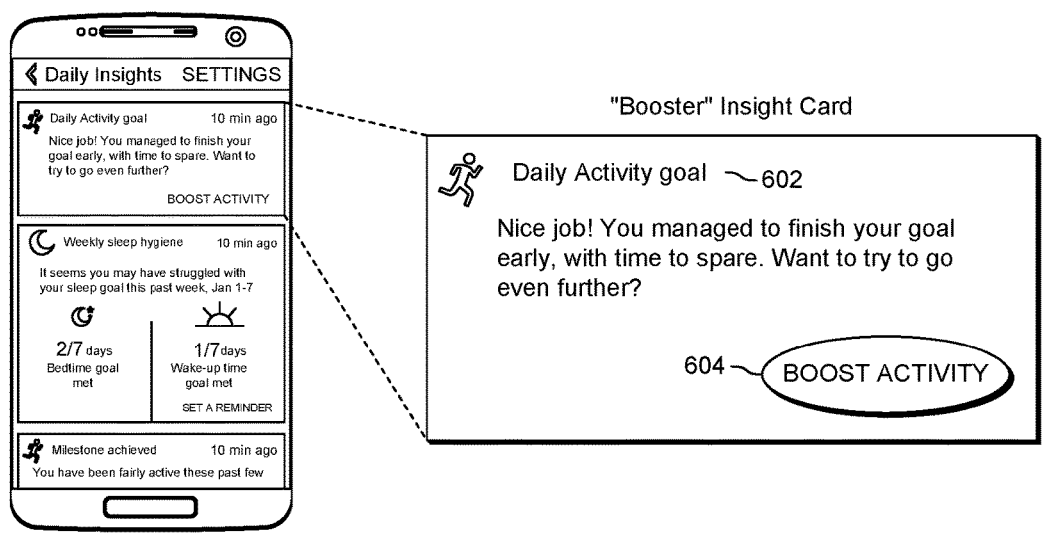
FIG. 6 is a diagram showing a mobile device displaying a daily activity goal.

Turning now to FIG. 6, a diagram shows a mobile device displaying another type of insight card that provides a daily activity goal 602. According to the example of FIG. 6, if the user accomplishes a certain goal of the user's wellness program, the user may be provided with a boost activity option 604, where additional actions related to the activity goal could be provided to help the user exceed the goal, or achieve a different goal that may be beneficial in the user's wellness program.

Figure 7:
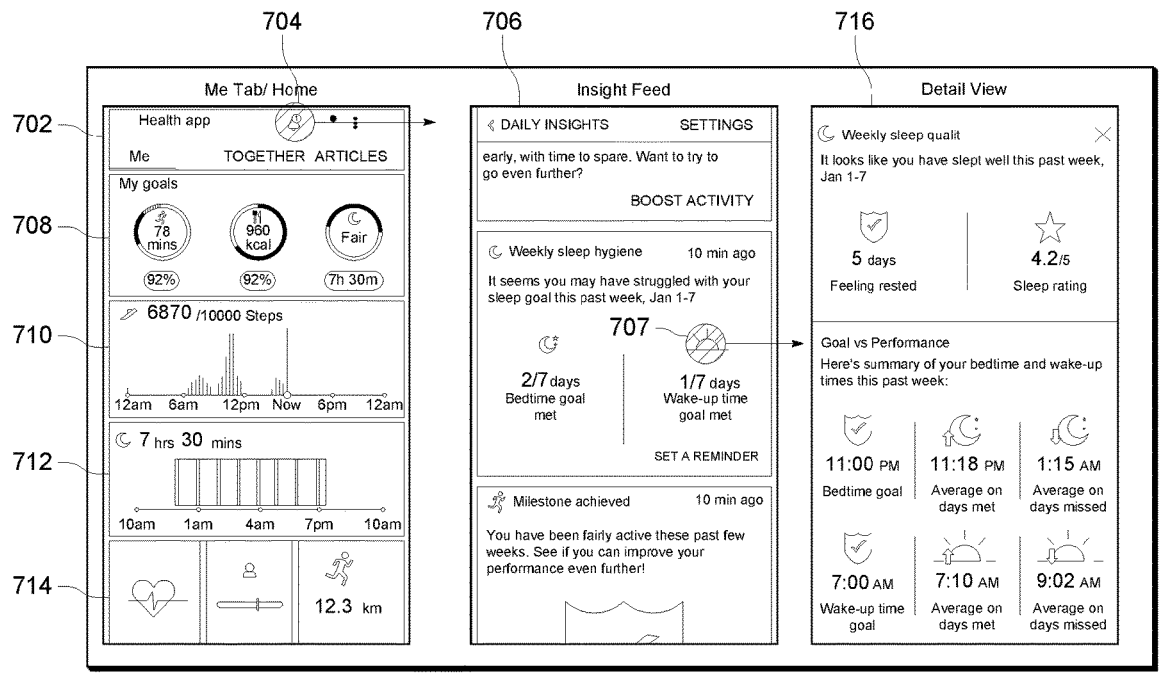
FIG. 7 is a diagram showing different levels of information accessible on a device providing insight information.

Turning now to FIG. 7, a diagram shows different levels of information accessible on a device providing insight information. As shown in FIG. 7, a main screen display 702 for a health tracking app comprises an daily insight feed icon 704 that can be selected to provide daily insights on the daily insights feed 706, as described above in reference to FIGS. 5 and 6. The main screen display 702 comprises a group of information sections, including by way of example a goal section 708, a step tracking section 710, and sleep monitoring section 712, and a sensor tracking section 714. When insight feed icon 704 is selected, the daily insights feed is presented, where different fields associated with daily insights could be accessed. By accessing a quick access panel 707 associated with a weekly sleep hygiene portion of the insights feed 706, the detailed view 716 shows data related to a user's sleep, including for example a sleep rating and sleep goals versus performance. While an example of a weekly sleep hygiene quick access panel is shown in FIG. 7 by way of example, it should be understood that quick access panels could be provided for any type of wellness information.

Figure 8:
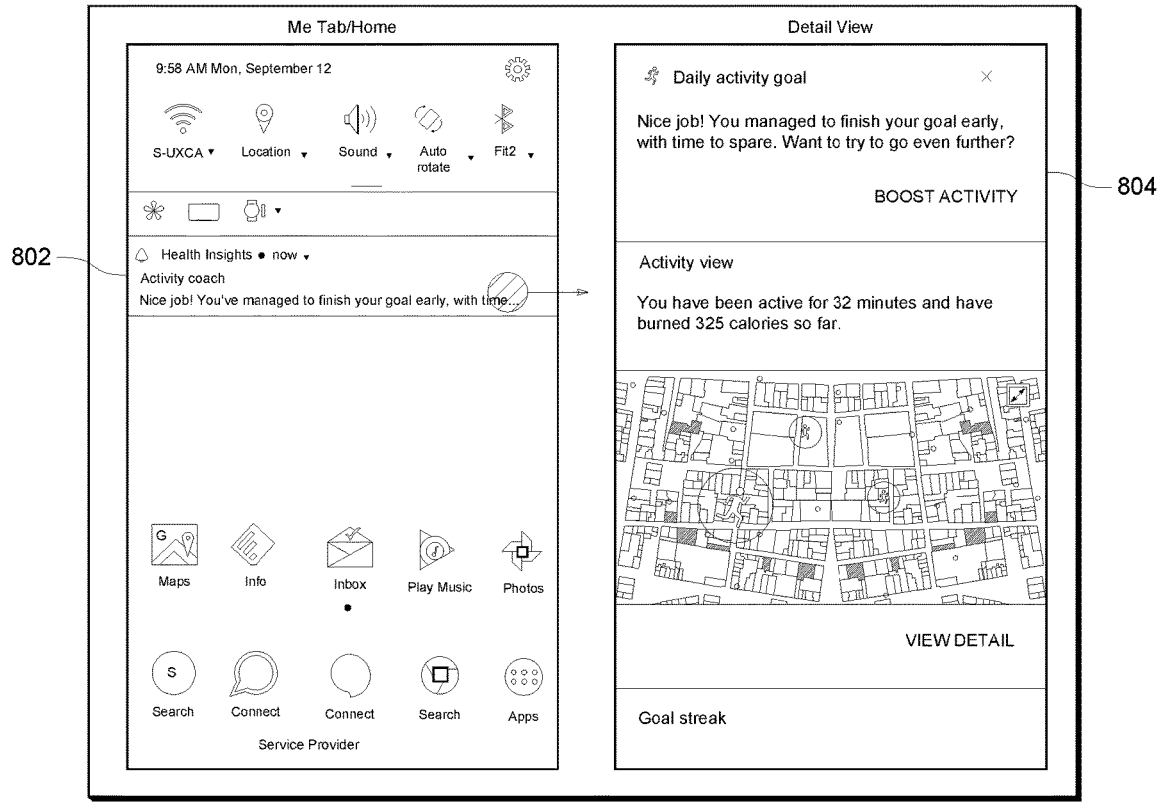
FIG. 8 is a diagram showing a device having a quick panel for providing information related to an activity goal.

Turning now to FIG. 8, a diagram shows a device having a quick access panel for providing information related to an activity goal. As shown in FIG. 8, an activity coach section 802 can be selected, where a daily activity goal 804 can be provided. The daily activity goal can include information related to an activity goal and include summary information associated with activity for achieving the goal. Within the daily activity goal, more detailed information can be provided in response to the selection of a category of summary data.

Figure 9:
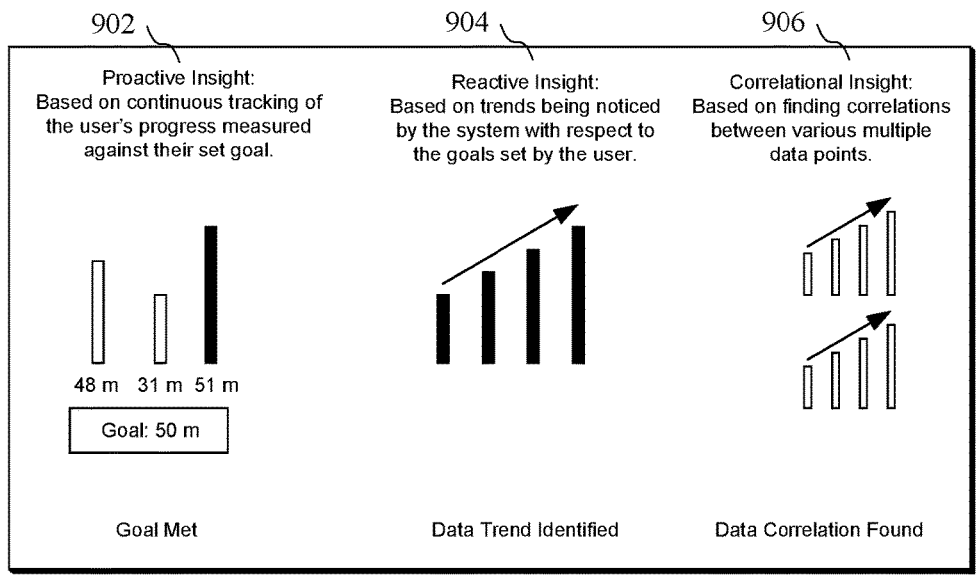
FIG. 9 is a diagram showing different categories of information provided to a user of a device tracking wellness information.

Turning now to FIG. 9, a diagram shows different categories of information provided to a user of a device tracking wellness information. The categories of information shown by way of example in FIG. 9 include proactive insight, reactive insight, and correlational insight as described above. According to the example of FIG. 9, the proactive insight may include an indication of a goal met for a certain category of activity, a reactive insight may include a particular data trend that is identified for a particular activity, and a data correlation. A summary of the insight could be presented, or the user could select the insight, such as by tapping the screen, to access more detailed information related to the insight.

Figure 10:
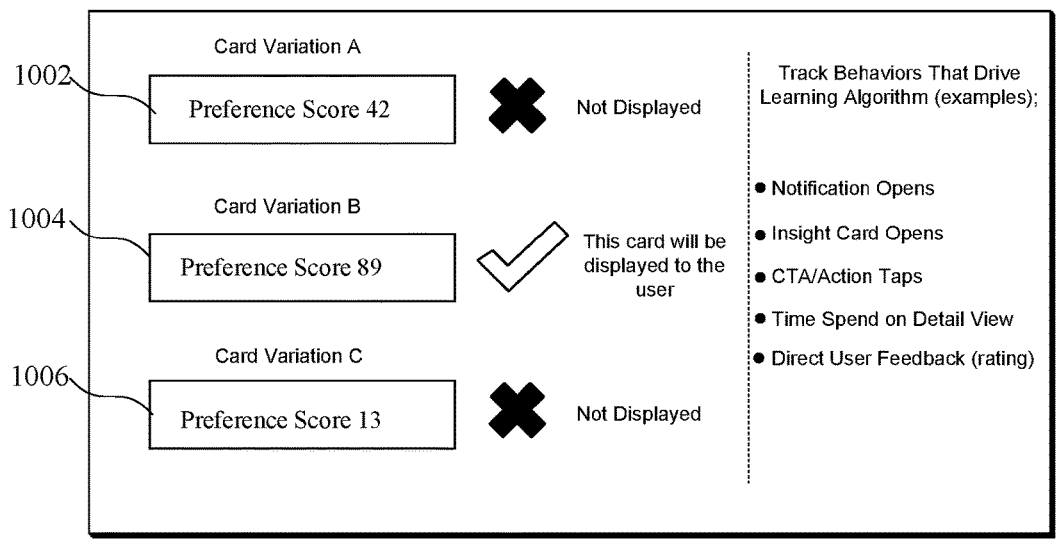
FIG. 10 is a diagram showing insight card variations and tracked behaviors that drive a learning algorithm.

As shown by way of example in FIG. 10, different variations of an insight card could be considered, where one particular card variation may be accepted based upon a score. According to the example of FIG. 10, 3 different insight card variations 1002-1006 could be considered, where one may be selected based upon a preference score. Insight card variation 1004 having the highest preference score of 89 may be selected according to this example. A number of different factors can be considered in determining a preference score, such as a number of times a type of notification is opened, a number of insight cards that are opened, CTA/Action Taps, the amount of time spent on Detail View, and direct user feedback (i.e. a rating). While this criteria for determining a preference score is provided by way of example, it should be understood that a fewer or greater number of criteria could be used, and the criteria could be weighted to generate a preference score.

Turning now to FIG. 11, a diagram shows the presentation of information associated with a time zone shift. As shown in FIG. 11, different fields related to a time zone shift could be provided. A goal portion 1102 could be provided to enable a user to review a goal related to achieving wellness goals in spite of time zone changes. A status portion 1104 could be provided to enable a user to understand information related to a potential future time zone change. For example, a device could detect that the user is moving or may have knowledge of travel plans based upon calendar information for example, and estimate the time zone change. A social insight 1106 could be provided based upon the time zone change, such as providing an indication of the most active time period for a user in the new time zone.

A Time Zone Insight may also allow using a user's location and time zone shift data to suggest adjusting their sleep and activity goals to optimize their health, recover from jetlag and maintain their progress towards their health goals. When a user travels and crosses time zones, a device will notify the user with activity recommendations based on recognition of such changes. Time zone shift notification and recommendation is one example of the proactive insight feature.

Upon recognition of a time zone change, the device may retrieve the user's wellness plan and identifies activities that should be carried out for the rest of the day. If the user is shadowing another user in a different time zone, it will alert the user and ask if the user would prefer to be temporarily matched with another user in the same time zone; if not, goals and challenge requests will be adjusted as necessary for the new time zone. In one embodiment, the device may prompt the user by asking whether she is interested in keeping the same time schedule for these activities, notwithstanding the time zone change. The device may recommend an adjusted activity schedule, changing activity period for one activity, removing one activity, and/or replace one activity with another, etc. The recommendation is based on the percentage needed to accomplish the goal set by the wellness plan for that day (e.g. where completion percentage can be determined based on already performed activities, which are tracked by the device, for that day), the remaining time for the day caused by the time zone change, the user's activity history and preference associated with the present time. The device may be configured to further recognize transportation modes, track food/water consumption. The device may also retrieve information identifying an impact (e.g. adjust jet lag that the user needs to sleep shorter/longer than usual, take certain medicine, etc.) to a human due to the time zone change. Considering such an impact with the other information described above, the device may recommend nutrition intake and other activities (e.g. unusual activities such as meditation, message; or activity specific to the present location of the user, surfing, skiing, etc.) to help the user stay on the wellness plan.

The following example shows Actionable Insights based upon a time zone change. Adam has a goal of sleeping at least 8 hours, with a bedtime of 10 pm and a wake-up time of 6 am set on his wellness application. User A embarks on a business trip to Dubai, where the time difference is +8 hours. Upon landing in Dubai, he receives an insight card that welcomes him to Dubai and reminds him of the time zone change. It asks him if he would like to be matched with a local user, and he consents. A local user in the new time zone could be selected to have similar characteristics as the user being followed in the original time zone. For example, the local user can be someone sharing similar fame/reputation, body shape, age, gender, etc., someone who has a good relationship with a particular user such as a celebrity, someone who has exercised or joined activity events previously with the celebrity, a trainer of the celebrity, or someone with profile similar to the user himself, etc. The local user in the new time zone could be selected based upon criteria for matching users, such as the use of a performance index as set forth below or any other criteria for matching a user to another user having similar goals or characteristics. A list of applicable users is generated, along with a list of local groups with information on their activities and historic data, and he selects the "Dubai Runners Club" group to shadow. Actionable Insights also provides him contextual data, including local sunrise and sunset, average statistics on sleep within that country and city, and number of daylight hours left. He is also presented with contextually-relevant articles that provide tips and guidance on how to improve the quality and duration of his sleep while he is traveling. It should be noted that the user can still follow the same celebrity, but based upon different criteria. Instead of following the celebrity's present activity, the user can participate in activities based on what the celebrity did when experiencing a similar time zone change. The user can also choose to participate in activities similar to other followers of the celebrity, current activities when they are in the same current time zone, or past activities when they were in the same time zone previously. An action may be presented on-screen to Adam to change his sleep goal. He taps the action button, allowing him to adjust his bedtime and wake-up time to more reasonable hours, allowing him to maintain his sleep goals in his new time zone. In one embodiment, Actionable Insights may make recommendations and/or provide insights without user inputs.

The device is also capable of providing advanced recommendation if it can determine that time zone change will happen within certain time period based on analyzing of the user's calendar (e.g. events listed on the calendar indicating traveling to a different city, state, or country).

Figure 12:
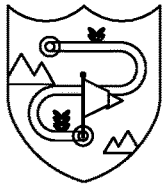
FIG. 12 is a diagram showing an activity summary for a user of a device tracking wellness information.

Turning now to FIG. 12, a diagram shows an activity summary for a user of a device tracking wellness information. A summary field 1202 could be included to provide a user with summary information, such as a weekly activity summary as shown. A performance field 1204 could be included to provide a user with information related to a user's performance, such as exercise, diet, or any other metric for determining a user's activity that may impact achieving a wellness goal. The performance field 1204 of FIG. 12 may include information related to a goal versus performance for certain activities and performance detail associated with certain days of a week for example.

All Actionable Insights are delivered to a user relative to their own goals, providing customized messages, content and recommendations dependent on how they perform against these benchmarks. Goals can be set manually, or through a mechanism known as "shadowing." Shadowing provides the user visibility into the health activities that another user is engaged in. Dependent on bi-directional preferences, users can see such items as but not limited to scheduled workouts, meal plans, and sleep schedules of the users they shadow. Importantly, users can set their own goals relative to a Shadowed user's goals, selecting either to match or outperform (i.e. "beat") these goals.

Users can shadow their immediate contacts, friends and family by directly connecting with them through a wellness tracking app. They can also ask to be algorithmically matched with another wellness tracking user who has a similar health profile (including for example weight, height, age, BMI, health goals and past performance), creating a "virtual" shadowing relationship with this user. The requested user has the option to share or not share their data and has complete control over what information is shared. Users can also shadow groups of people, such as their home town (e.g. Sunnyvale, Calif.) or affinity groups (e.g. "Sea Kayakers"). Finally, users can shadow celebrities or well-known personalities, either for free or for a fee.

Users can be matched with another user of a wellness tracking app using a number of data inputs, which together yield a "performance index" that is not visible to the user but that presents a number of recommended users to shadow. The inputs that matching takes into account include: self-reported data: health goals, level of desired effort, functional training requirements, if any. Data can also include automatically collected data, such as time zone and location type (e.g. urban, suburban, exurban or rural), training or activity history, weather, transaction history (e.g. a mobile payment vendor), content consumption patterns (e.g. TV, radio, music, etc.), driving habits and patterns (e.g. collected via Automatic or similar device), keywords/topics discussed (e.g. collected via connected speaker or similar device), usage of home devices, such as thermostat, kitchen appliances, etc., device purchases, apps on device. When one user shadows another, they may have access to a dashboard of the user that looks similar to his own within a wellness tracking app, showing step counts, sleep activity, food log, etc. They can also "Mirror" their health goals, resetting their active goals to match exactly the goals of the shadowed user. They can also "compete" with the user, deciding by what percentage they would like to exceed their goals (and in which direction). They can "challenge" this user to a specific workout or activity, such as a run, which sends a request to this user to accept or reject the challenge. Finally, users may have access to a "feed" of all the activities of the users they follow, keeping up-to-date with their progress against their health goals. Any of the information provided above is available to a user who is shadowing another user.

The following flow charts describe various exemplary methods of allowing a user to receive information associated with a wellness program. The various elements of the methods of FIGS. 13-17 may be implemented using the systems and circuits of FIGS. 1-12 as described, or using some other suitable circuits. While specific elements of the method are described, it should be understood that additional elements of the method, or additional details related to the elements, could be implemented according to the disclosure of FIGS. 1-12.

Figure 13:
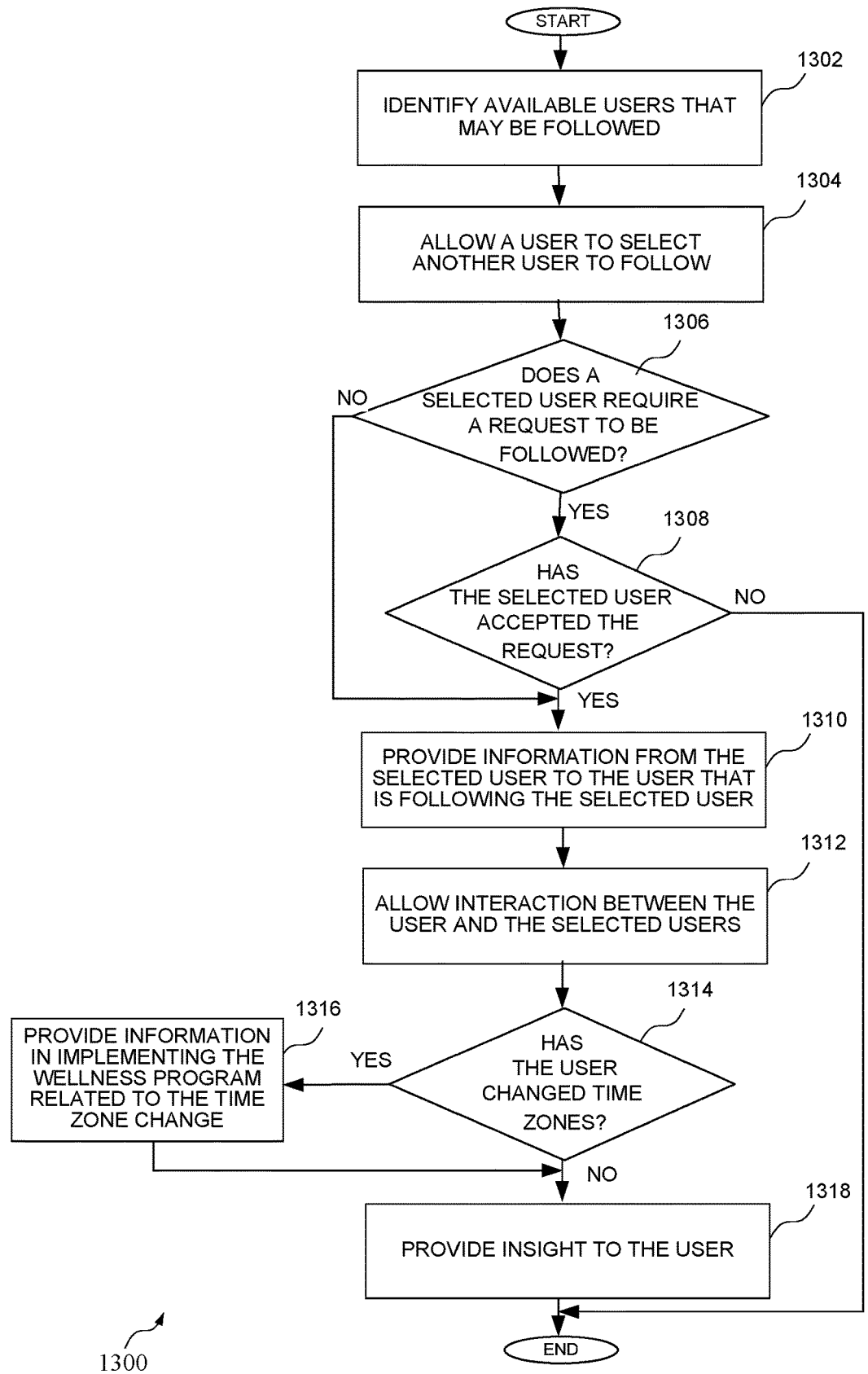
FIG. 13 is a flow diagram showing an exemplary method of allowing a user of a device tracking wellness information to shadow another user of a device tracking wellness information.

Turning first to FIG. 13, a flow diagram shows a method of allowing a user of a device tracking wellness information to shadow another user of a device tracking wellness information. Available users that may be followed are identified at a block 1302. A user is allowed to select another user to follow at a block 1304. The user may select another user to follow on a mobile device or other computer device using a wellness app for example. It is then determined whether a selected user is required to receive a request to be followed at a block 1306. Such a requirement may be set by a user on a mobile device or other computer implementing a wellness app. If so, it is determined whether the selected user has accepted the request at a block 1308. Information from the selected user is provided to the user that is following the selected user at a block 1310.

Interaction between the user and the selected user is allowed at a block 1312. It is then determined whether the user has changed time zones at a block 1314. By way of example, the various users may exchange messages related to their shadowing. Information in implementing the wellness program related to the time zone change is provided at a block 1316. Insight is provided to the user at a block 1318. For example, any type of insight as described above could be provided.

Figure 14:
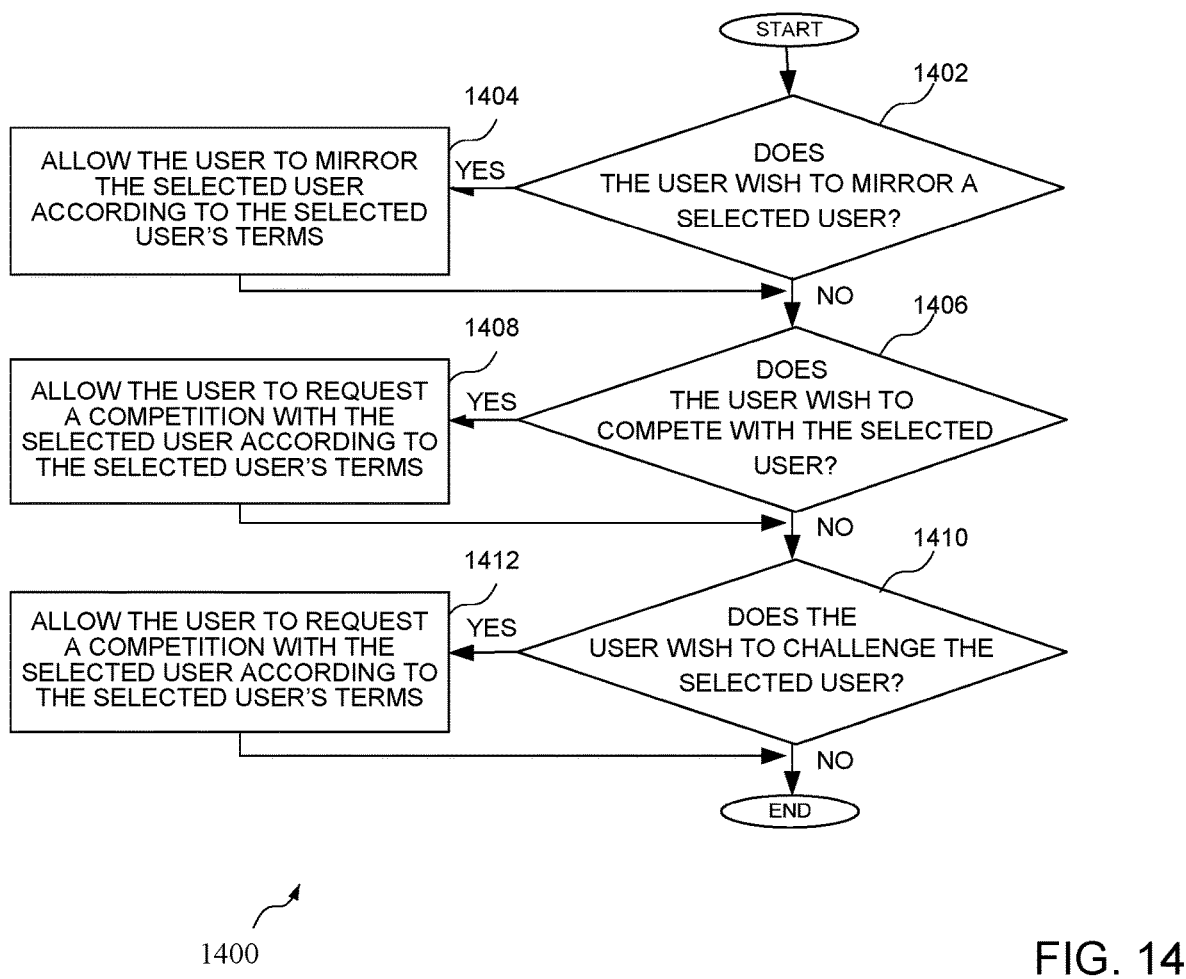
FIG. 14 is a flow diagram showing an exemplary method of enabling a user that is being shadowed to establish rules related to the transfer of information.

Turning now to FIG. 14, a flow diagram shows a method of enabling a user that is being shadowed to establish rules related to the transfer of information. It is determined whether the user wishes to mirror a selected user at a block 1402. If so, the user is allowed to mirror the selected user according to the selected user's terms at a block 1404. For example, a user that is being followed can select what type of information is provided to the other user. It is then determined whether the user wishes to compete with the selected user at a block 1406. If so, the user is allowed to request a competition with the selected user according to the selected user's terms at a block 1408. For example, the user that is being followed may select the type of activities that she may wish to compete in (e.g. number of steps, hours of exercise per week, etc.). It is also determined whether the user wishes to challenge the selected user at a block 1410. If so, the user is allowed to request a competition with the selected user according to the selected user's terms at a block 1412. For example, the user may select to be provided a request only on week on weekends or during the summer.

Figure 15:
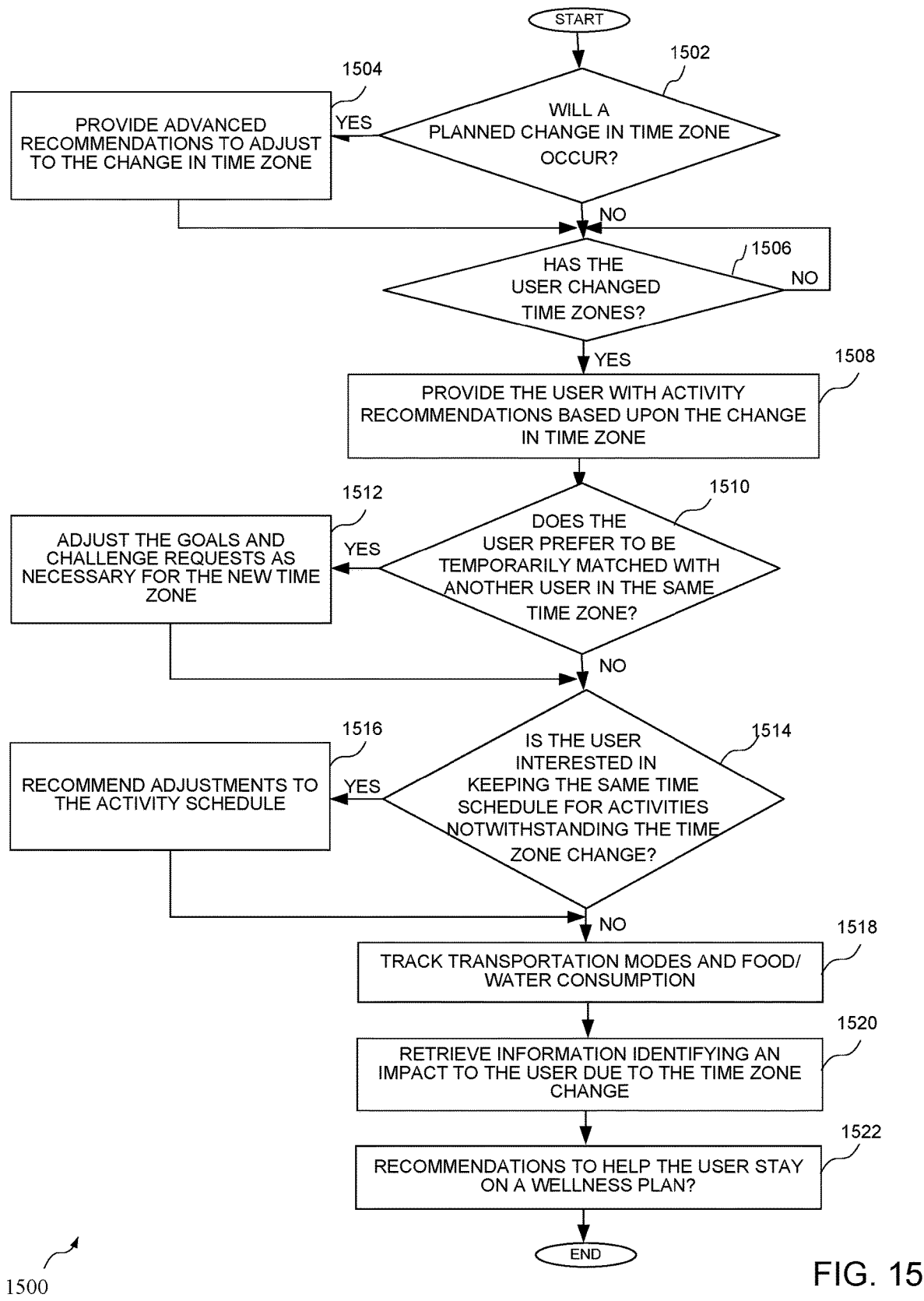
FIG. 15 is a flow diagram showing an exemplary method of providing information to a user of a device tracking wellness information based upon changes in a time zone.

Turning now to FIG. 15, a flow diagram shows a method of providing information to a user of a device tracking wellness information based upon changes in a time zone. It is determined whether a planned change in time zone will occur at a block 1502. If so, advanced recommendations are provided to adjust to the change in time zone at a block 1504. It is then determined whether the user has changed time zones at a block 1506. If so, the user is provided with activity recommendations based upon the change in time zone at a block 1508. It is also determined whether the user prefers to be temporarily matched with another used in the same time zone at a block 1510. If so, the goals and challenge requests are adjusted as necessary for the new time zone at a block 1512. It is also determined whether the user is interested in keeping the same time schedule for activities notwithstanding the time zone change at a block 1514. If so, recommendations to adjustments to the activity schedule are made at a block 1516. Transportation modes and food/water consumption may be tracked at a block 1518. Such information may help determining whether to provide an insight into a user to prevent and accident or prevent dehydration. Information identifying an impact to the user due to the time zone change may be retrieved at a block 1520. Recommendations to help the user stay on a wellness plan may also be made at a block 1522.

Figure 16A:
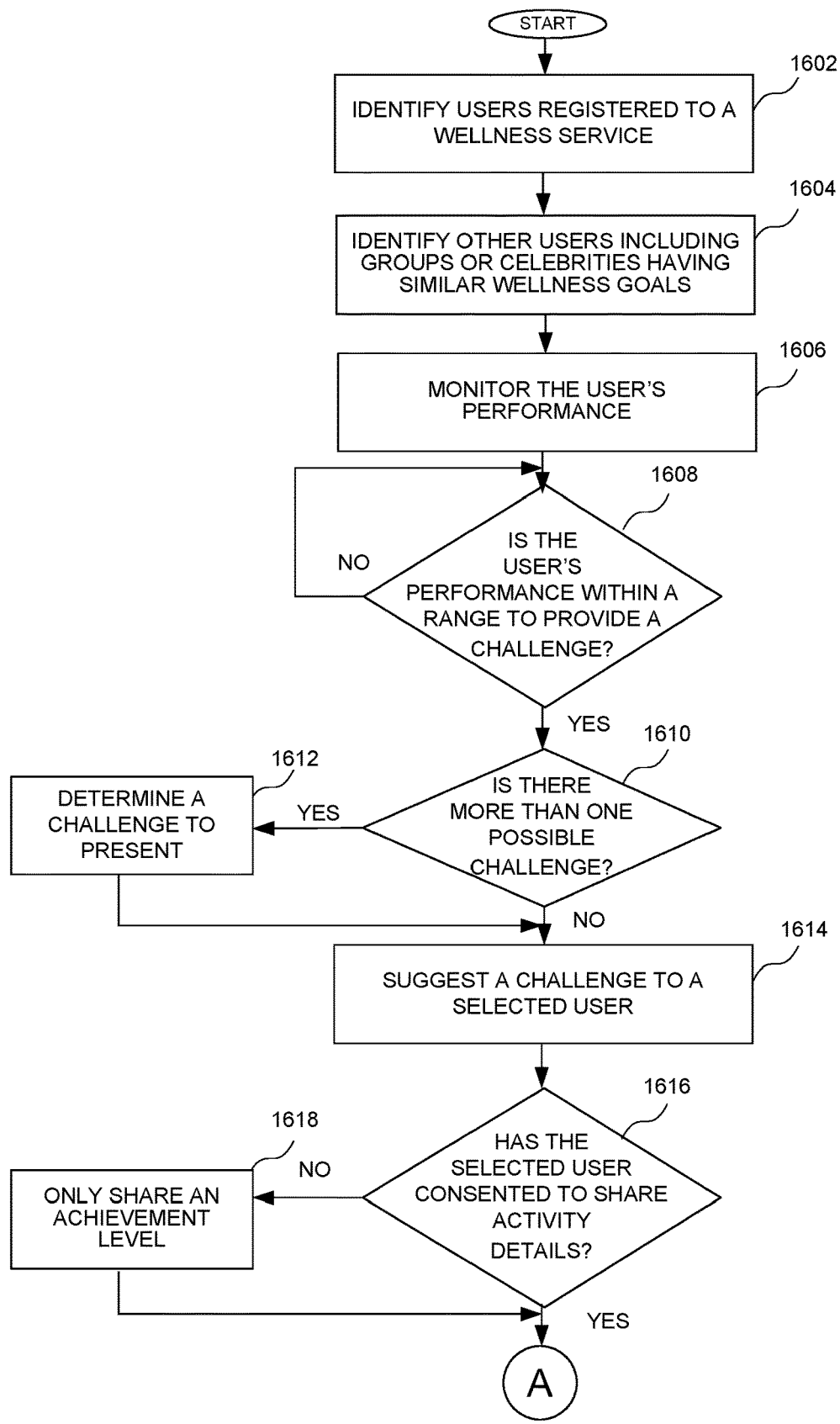
FIG. 16 including a first part FIG. 16A and a second part
FIG. 16B is a flow diagram showing an exemplary method of providing information to a user of a device related to social insight.
Figure 16B:
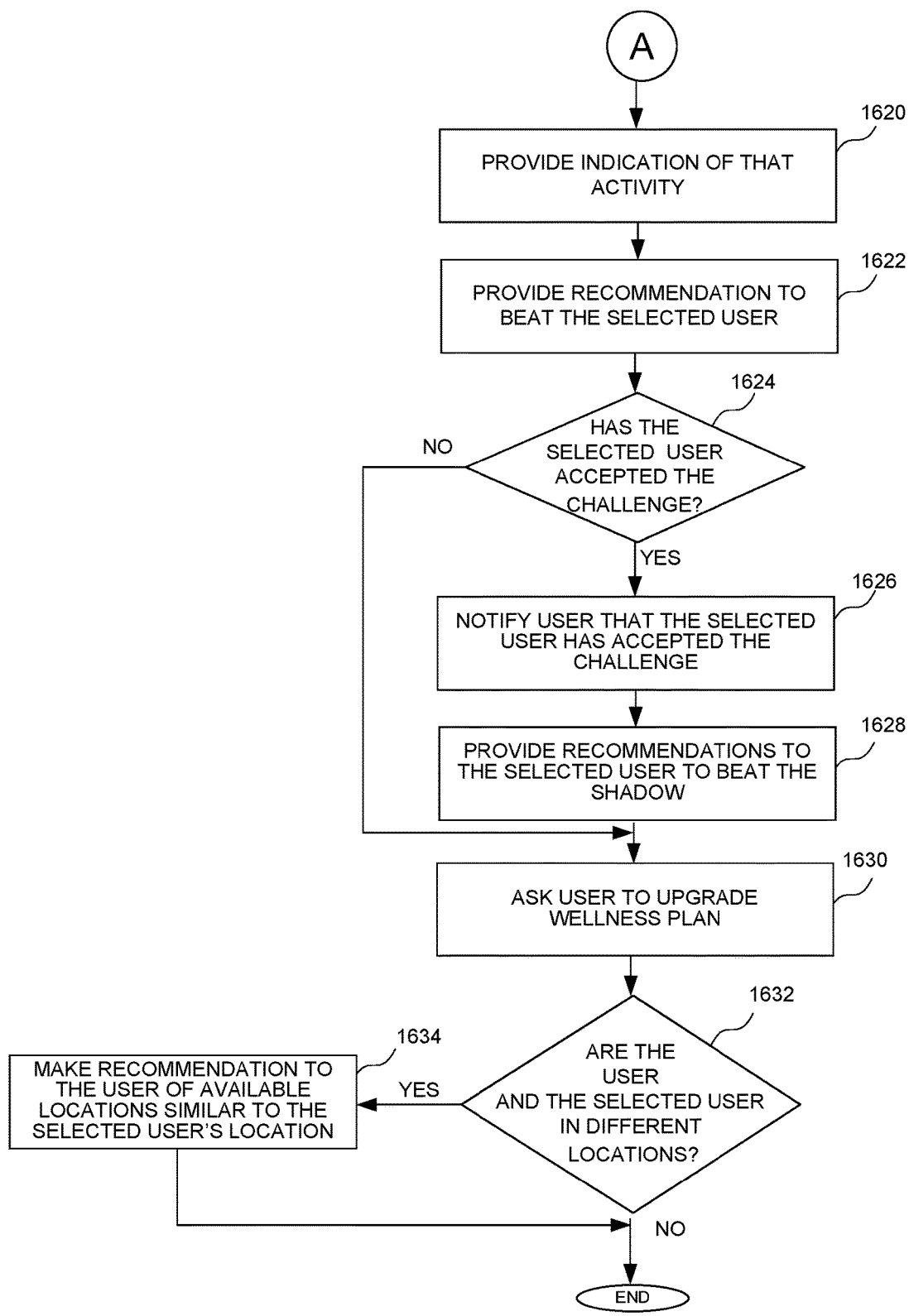

Turning now to FIG. 16, a flow diagram shows a method of providing information to a user of a device related to social insight. Users registered to a wellness service are identified at a block 1602. Other users including groups or celebrities having similar wellness goals are identify at a block 1604. A user's performance is monitored at a block 1606. It is then determined if a user's performance within a range to provide a challenge at a block 1608. If so it is also determined if there is more than one possible challenge at a block 1610. If so, a challenge to present is determined at a block 1612. Either way, a challenge is suggested to a user at a block 1614.

It is then determined whether the selected user has consented to share activity details at a block 1616. If not, only limited information may be shared, such as an achievement level at a block 1618, and an indication of that activity is provided at a block 1620. A recommendation to beat the selected user is provided at a block 1622. It is determined whether the selected user has accepted the challenge at a block 1624. If so, the user is notified that the selected user has accepted the challenge at a block 1626. Recommendations are provided to the selected user to beat the user at a block 1628. The user can then be asked to upgrade a wellness plan at a block 1628. It is also determined whether the user and the selected user are in different locations at a block 1630. If so, a recommendation may be made to the user of available locations similar to the selected user's location at a block 1632.

Figure 17A:
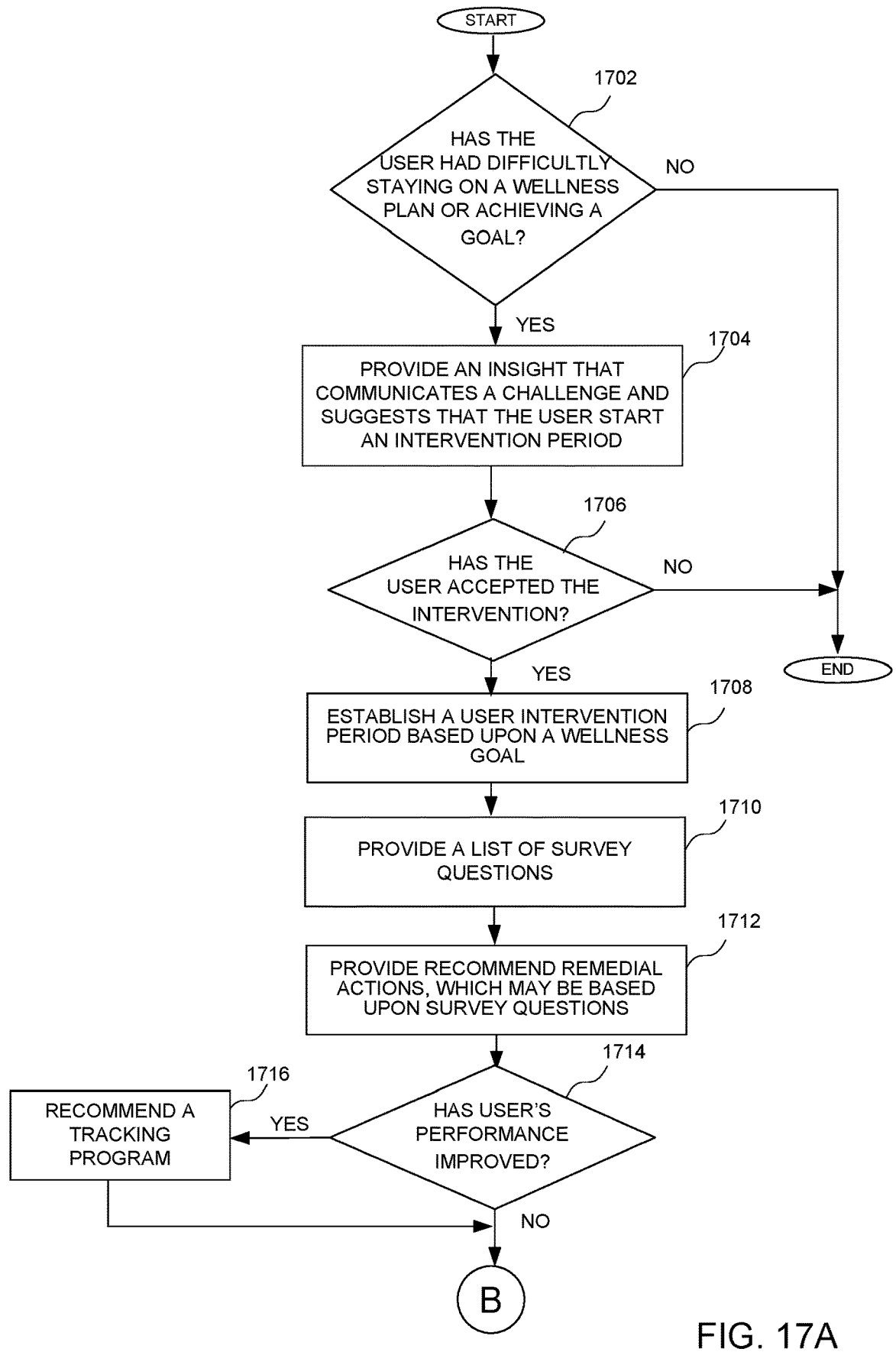
FIG. 17 including a first part FIG. 17A and a second part
FIG. 17B is a flow diagram showing an exemplary method of enabling an intervention based upon information associated with activities of a user trying to achieve a wellness goal.
Figure 17B:
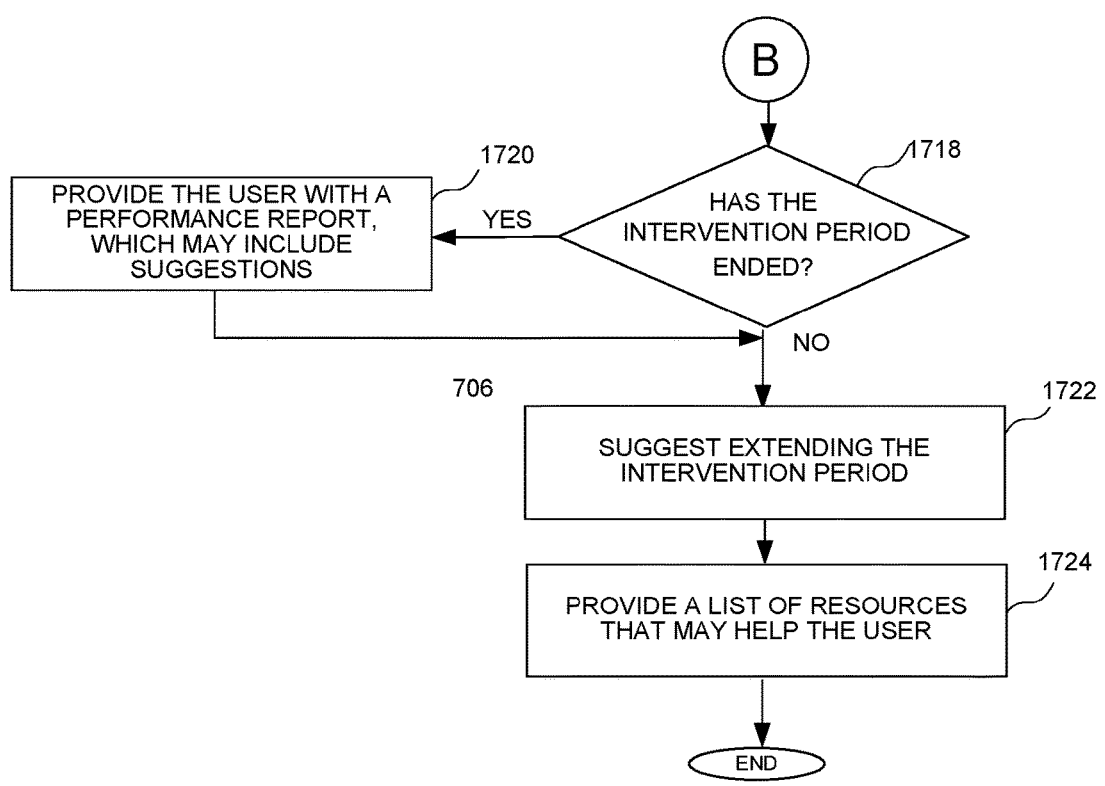

Turning now to FIG. 17, a flow diagram shows a method of enabling an intervention based upon information associated activities of a user trying to achieve a wellness goal. It is determined whether the user has had difficulty staying on a wellness plan or achieving a goal at a block 1702. If so, an insight that communicates a challenge and suggests that the user start an intervention period is provided at a block 1704. It is then determined whether the user has accepted the intervention at a block 1706. If so, a user intervention period based upon the wellness goal is established at a block 1708. A list of survey questions are provided at a block 1710. Remedial actions, which may be based upon survey questions, may also be provided at a block 1712.

It is then determined whether the user's performance has improved at a block 1714. If so, a tracking program may be recommended at a block 1716. It is also determined whether the intervention period has ended at a block 1718. If so, the user may be provided with a performance report, which may include suggestions to achieve performance goals, at a block 1720. If not, it may be suggested to extend the intervention period at a block 1722, and a list of resources that may help the user may be provided at a block 1724.

It can therefore be appreciated that new systems for and methods of allowing a user to receive information associated with a wellness goal has been described. It will be appreciated by those skilled in the art that numerous alternatives and equivalents will be seen to exist that incorporate the disclosed invention. As a result, the invention is not to be limited by the foregoing implementations, but only by the following claims.

We claim:

1. A method of allowing a user, using a mobile device, to receive information associated with a goal, the method comprising:
   detecting, using a processor circuit of the mobile device, a change in a time zone of the user;
   combining multiple user data points including user goals and sensor data to generate a correlation between the multiple user data points and achieving the goal in the time zone;
   identifying at least one other user from a list of users in the time zone based upon the correlation between the multiple user data points and achieving the goal in the time zone;
   presenting, on a display of the mobile device, the at least one other user for the user to follow based upon a location of the user and a location of the at least one other user in the time zone;
   allowing, using the processor circuit of the mobile device, the user to select the at least one other user to compare information of the user to information of the at least one other user;
   providing, to the user, the information of the at least one other user related to activities of the at least one other user, wherein the information of the at least one other user is used to adjust the goal of the user based upon the change in the time zone of the user;
   monitoring interactions of the user with information that is provided to the user, wherein the monitoring is based upon at least one of time spent viewing the information that is provided to the user or a selection of the information that is provided to the user using user interface elements of the mobile device; and
   presenting the information associated with the goal to the user, wherein the information associated with the goal is based upon the monitoring of the interactions of the user with the information provided to the user, and information that is viewed or selected by the user is prioritized and displayed.

2. The method of claim 1 further comprising providing a request to be followed to the at least one other user.

3. The method of claim 1 wherein presenting the at least one other user comprises presenting other users of mobile devices having similar goals.

4. The method of claim 1 further comprising providing a challenge to the user based upon a performance measurement of the at least one other user.

5. The method of claim 4 wherein providing a challenge to the user comprises determining when a performance measurement of the user is within a predetermined range of the performance measurement of the at least one other user.

6. The method of claim 1 wherein the goal presented to the user is based upon whether the user has found the goal useful in the past.

7. The method of claim 1 wherein the goal is presented based upon how many goals have been presented.

8. A method of allowing a user, using a mobile device, to receive information associated with a wellness goal, the method comprising:
   detecting, using a processor circuit of the mobile device, a change in a time zone of the user;

combining multiple user data points including user goals and sensor data to generate a correlation between the multiple user data points and achieving the wellness goal in the time zone;

identifying at least one other user from a list of users in the time zone that is tracking wellness information based upon a location of the user and a location of the at least one other user and based upon the correlation between the multiple user data points and achieving the wellness goal in the time zone;

determining whether a wellness measurement associated with a wellness goal of the at least one other user that is tracking wellness information is within range of a wellness measurement associated with the wellness goal of the user;

monitoring interactions of the user with information associated with the wellness goal of the user, wherein the monitoring is based upon at least one of time spent viewing information associated with the wellness goal or a selection of information associated with the wellness goal using user interface elements of the device; and providing, using a processor of the mobile device, a challenge to the user to achieve a different wellness goal based upon the wellness measurement associated with the wellness goal of the at least one other user and the change in the time zone of the user;

wherein information associated with the different wellness goal is based upon a monitoring of the interactions of the user with the information associated with the wellness goal of the user; and wherein information that is viewed or selected by the user is prioritized and displayed.

9. The method of claim 8 further comprising allowing the user to select the at least one other user to compare wellness information.

10. The method of claim 9 further comprising providing a request from the user to the at least one other user to follow the at least one other user.

11. The method of claim 8 wherein determining whether a wellness measurement associated with a wellness goal of the at least one other user is within range of the wellness measurement associated with a wellness goal of the user comprises identifying a preferred user of a plurality of users having a wellness measurement within range of the user.

12. The method of claim 8 further comprising sharing information related to the wellness measurement of the at least one other user with the user.

13. The method of claim 8 wherein providing the challenge to the user comprises providing the challenge to the user based upon a preference score.

14. The method of claim 13 wherein the preference score is based upon a number of times that a challenge has been opened.

15. The method of claim 8 further comprising:
determining whether the user has failed to achieve the wellness goal;
initiating an intervention period to help the user to achieve the wellness goal; and
providing a recommendation to the user to achieve the wellness goal.

16. The method of claim 15 wherein initiating an intervention period to help the user to achieve the wellness goal comprises providing an invitation to the user to participate in the intervention period.

17. The method of claim 15 further comprising providing survey questions to allow remedial action recommendations to be sent in the intervention period.

18. The method of claim 15 further comprising recommending a tracking program when the user is making progress in achieving the wellness goal.

19. The method of claim 15 further comprising determining if the intervention period should be extended before the intervention period has expired.

20. The method of claim 15 further comprising providing the user with a performance report associated with the intervention period.

\* \* \* \* \*